United States Patent [19]

Venkatram et al.

[11] 4,219,675
[45] Aug. 26, 1980

[54] BATCH PROCESS FOR MANUFACTURING AND PURIFYING LIQUID ORGANIC PEROXIDE BY DISTILLATION

[75] Inventors: Ramdas Venkatram; Vasanth R. Kamath, both of Tonawanda, N.Y.; Chester J. Smith, Crosby, Tex.

[73] Assignee: Pennwalt Corporation, Philadelphia, Pa.

[21] Appl. No.: 9,895

[22] Filed: Feb. 6, 1979

[51] Int. Cl.$^2$ .................. C07C 179/10; C07C 179/18
[52] U.S. Cl. ................................ 568/563; 568/562; 260/453 RZ; 260/463
[58] Field of Search ............... 568/562, 576, 568, 563, 568/566; 260/453 R, 453 RZ, 463

[56] References Cited

U.S. PATENT DOCUMENTS

| | | | |
|---|---|---|---|
| 3,082,236 | 4/1959 | Maglie et al. | 568/561 |
| 3,117,166 | 1/1964 | Harrison et al. | 568/561 |
| 3,138,627 | 6/1964 | Harrison et al. | 568/561 |
| 3,435,060 | 3/1969 | Johannes | 260/453 |
| 3,849,468 | 11/1974 | Busseret | 260/463 |
| 3,869,489 | 11/1974 | Busseret | 568/566 |
| 4,075,236 | 2/1978 | Wagle | 568/561 |

FOREIGN PATENT DOCUMENTS 1251042  10/1971  United Kingdom ............ 568/561

*Primary Examiner*—Werren B. Lone

[57] ABSTRACT

A batch process for the manufacture of liquid organic peroxides, such as peroxy esters and diacyl peroxides, by reacting an acid chloride, a hydroperoxide and an alkali metal hydroxide uses a countercurrent, packed distillation column for recovering a purer, drier product with higher yield than previous batch drying processes.

3 Claims, 2 Drawing Figures

BATCH PROCESS FOR MANUFACTURING AND PURIFYING LIQUID ORGANIC PEROXIDE BY DISTILLATION

BACKGROUND OF THE INVENTION

This invention concerns a process and apparatus for the batch manufacturing and purifying of liquid organic peroxides resulting in increased yields, drier, purer and more active product and less pollution of the environment. More particularly, this invention relates to the recovery of liquid peroxy esters and diacyl peroxides from a batch process by countercurrent convective distillation.

Prior art batch processes for the manufacture of liquid organic peroxides, especially peroxy esters and diacyl peroxide, generally make use of chemical drying agents such as anhydrous magnesium or sodium sulfate and the like. Disadvantages of using this conventional inorganic drying agent are that the drying agent is difficult to separate from the product resulting in an impure product with a low yield. Disposing of the sulfate drying agents also creates a problem since it has become an undesirable pollutant in the environment, especially in lakes and rivers. The product also contains a high percentage of water. For example, see U.S. Pat. Nos. 3,138,627, 3,082,236, 3,117,166, 3,435,060 and 3,869,489. British Pat. No. 1,251,042 describes a process for drying a liquid organic peroxide or an organic solution of an organic peroxide that uses a microporous filter cartridge to remove suspended aqueous liquid. U.S. Pat. No. 4,075,236 describes a continuous solvent free process for the manufacture of peroxy esters. This patent differs from the instant application since it is a continuous method using a more complicated system of at least two reactors with more energy input per unit of reactor for agitation than the instant application.

SUMMARY OF THE INVENTION

This invention is directed to a batch process for the manufacture of a peroxy compound having the formula

$(R)_y$—$(COO)_n(R')_x$ wherein:

(a) x, y and n are 1 or 2;
(b) when x is 2, y is 1 and n is 2;
(c) when y is 2, x is 1 and n is 2;
(d) when x, y and n are 1, R is selected from the group consisting of a primary, secondary or tertiary alkyl of 1–17 carbons, aryl of 6–14 carbons, and cycloalkyl of 3–12 carbons, said alkyl and cycloalkyl groups may be substituted by halogen, alkoxy or aryl, said aryl group may be substituted by halogen, alkoxy or alkyl; and R' is selected from the group consisting of tertiary alkyl of 4–12 carbons, tertiary aralkyl of 9–18 carbons, tertiary cycloalkyl of 6–12 carbons and

$R_1C$— wherein $R_1$ is independently selected from the definition of R except for tertiary-alkyl;

(e) when x is 2, R is a diradical selected from the group consisting of alkylene of 1–16 carbons, arylene of 6–14 carbons, cycloalkylene of 3–12 carbons and aralkylene of 7–18 carbons, and R' is the same as (d) except for

$R_1C$—;

and
(f) when y is 2, R' is a ditertiary diradical selected from alkylene of 6–16 carbons, aralkylene of 12–18 carbons, cycloalkylene of 7–12 carbons and alkynylene of 6–16 carbons, and R is the same as (d); which comprises:

1. Charging a batch reactor with

$R(CCl)_n$ and $R^1(OOH)_n$ in molar equivalent proportions selected from the group consisting of:

(i) 0.9 to 1.1 molar equivalents of

$RCCl$ and 0.4 to 0.6 molar equivalent of $H_2O_2$ or 0.9 to 1.1 molar equivalent of $R^1OOH$ or

$R_1COOH$, (ii) 0.9 to 1.1 molar equivalent of

$RCCl$ and 0.4 to 0.6 molar equivalent of $R^1(OOH)_2$, and
(iii) 0.9 to 1.1 molar equivalent of

$R(CCl)_2$ and 1.8 to 2.2 molar equivalent of $R^1OOH$ and an amount of an aqueous alkali metal hydroxide to maintain a pH greater than 10 and reacting this bath while stirring at a temperature range of about $-10°$ C. to $+50°$ C. for a sufficient time to complete the reaction; and 2. washing the reaction mass with an aqueous solution to remove impurities from the liquid organic product and to adjust the pH to neutral; the improvement which comprises:

3. purifying the liquid organic product in a countercurrent packed distillation column wherein the crude product is dispersed at the top of the column over the column packing and the purified product is removed from the bottom of the column, the crude product is countercurrently contacted with air or an inert gas admitted to the bottom of the column above a product sump in the bottom of the column wherein the product is maintained at a desired level to prevent exhaust of air at the bottom. The overhead gas stream is released to the atmosphere. The ratio of the downwardly flowing crude product to the upwardly flowing air or inert gas depends on the nature of the product being purified.

4. Optionally, passing the purified product through a polishing filter to remove the residual suspended solids left behind by the evaporation of moisture in the purification process.

DETAILED DESCRIPTION OF THE INVENTION

Figure 1:
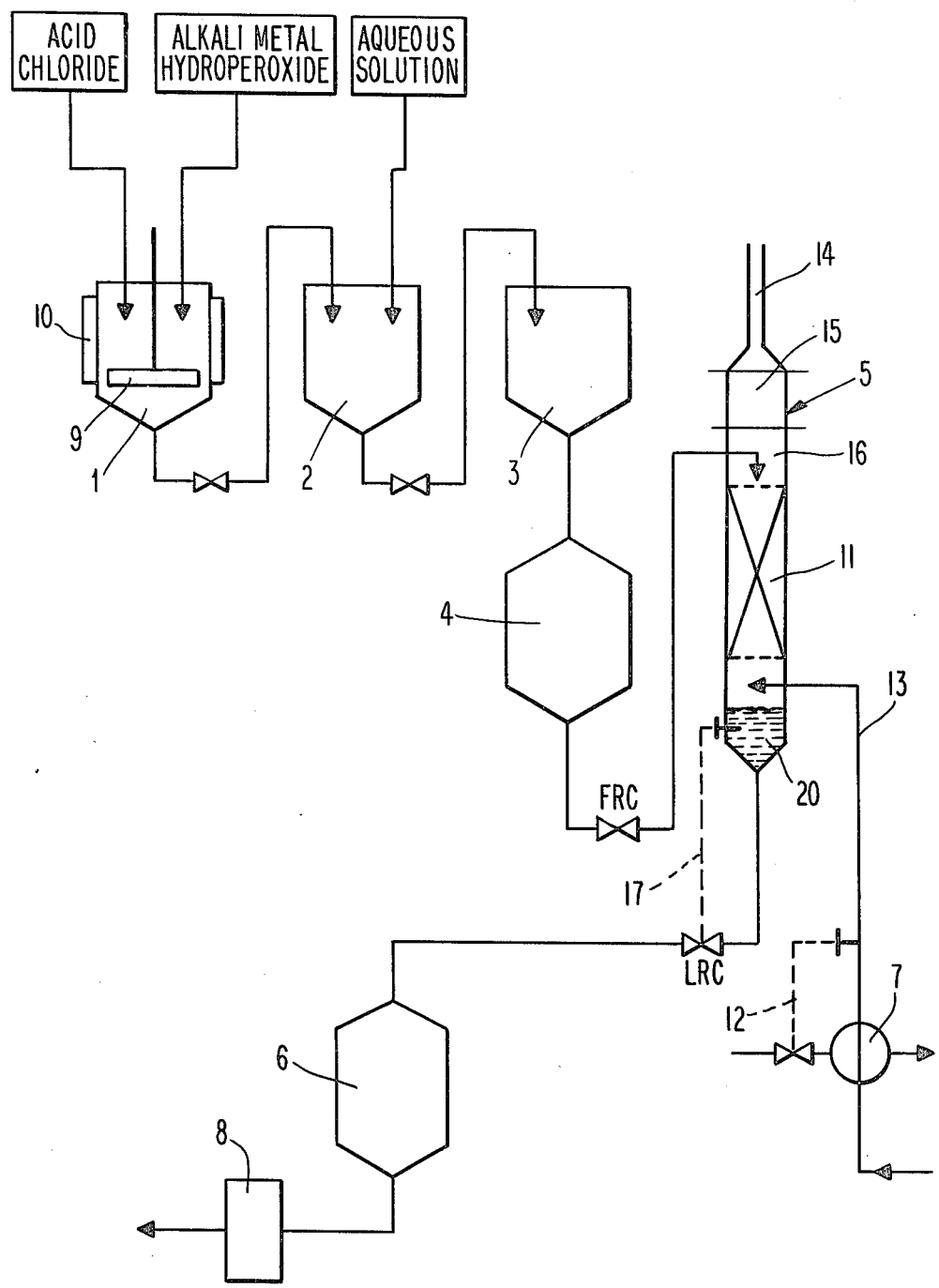

It has now been discovered that the impurities present in liquid organic peroxides and their solutions made via batch processes can be effectively removed in a safe manner with no environmental pollution by countercurrent convective distillation to generate a product of better quality than that obtained by prior art techniques. The process employs a distillation column either packed column or trays (bubble cap trays, sieve tray, etc.), at or below atmospheric pressure, wherein the crude product is brought in countercurrent contact with air or an inert gas which drives off the volatile impurities yielding a purified product which is then optionally passed through a polishing filter which removes the suspended solids to generate a pure, crystal clear product.

Examples of hydroperoxides $R'(OOH)_n$ useful in the process of this invention are:

(a) In the preparation of monoperoxyesters that is x, y and n=1 wherein the radical $R'$ and the hydroperoxide have the same name, t-butyl, t-amyl, t-hexyl, t-heptyl, t-octyl, cumyl, p-phenylcumyl, p-menthane(p-menthanyl), pinane (pinanyl), 1-methylcyclopentyl, and 1-methylcyclohexyl hydroperoxides;

(b) In the preparation of diperoxyesters that is y=2, x=1, n=2 and $R'$ is a diradical; 2,5-dimethyl-2,5-dihydroperoxyhexane ($R'$=1,1,4,4 tetramethyltetramethylene), 2,7-dimethyl-2,7-dihydroperoxyoctane ($R'$=1,1,6,6-tetramethylhexamethylene), 3,6-dimethyl-3,6-dihydroperoxyoctane ($R'$=1,4-dimethyl-1,4-diethyltetramethylene), 2,5-dimethyl-2,5-dihydroperoxyhexyne-3 ($R'$=1,1,4,4 tetramethyl-2-butynylene), and diisopropylbenzene dihydroperoxide ($R'=\alpha,\alpha,\alpha',\alpha'$-tetramethylxylylidene).

Examples of the alkali metal hydroxide used in the reactions are sodium hydroxide and potassium hydroxide.

Examples of the acid chlorides, $R(C(O)Cl)_n$, useful in the process of this invention are:

(a) In the preparation of monoperoxyesters (that is x, y and n=1); acetyl (R=methyl), propionyl (R=ethyl), butyryl (R=propyl), pentanoyl or valeroyl (R=butyl), 2-ethylhexanoyl (R=3-heptyl), isobutyryl R=isopropyl), 2-methyl-butyryl (R=sec-butyl), 2-methyl-pentanoyl (R=2-pentyl), 2-ethylbutyryl (R=3-pentyl), neodecanoyl (R=tertiary-nonyl), decanoyl (R=nonyl), lauroyl (R=undecyl), benzoyl (R=phenyl), toluoyl (R=methylphenyl), isononanoyl (R=2,-4,4-trimethyl-pentyl), naphthoyl (R=naphthyl), and pivaloyl (R=tertiary-butyl).

(b) In the preparation of diperoxyesters (that is xt32 2, y=1, n=2 and R is a diradical); malonyl (R=methylene), succinoyl (R=ethylene), glutaroyl (R=trimethylene), adipoyl (R=tetramethylene), azelaoyl (R=heptamethylene), sebacoyl (R=octamethylene), phthaloyl (R=o, m, p-phenylene) and fumaroyl (R=ethenylene).

(c) In the preparation of diacyl peroxides, acetyl, propionyl, butyryl, isobutyryl, pentanoyl, pelargonyl, hexanoyl, acetyl propionyl, acetyl pentanoyl, 2-methylpentanoyl, acetyl 2-chloropropionyl, acetyl 2-chlorobutyryl, 2chlorobutyryl 2-chlorobutyryl m-chlorobenzoyl, isononanoyl (3,5,5-trimethylhexanoyl), acetyl 3,5,5-trimethylhexanoyl, decanoyl.

Illustrative of but not limiting of the various liquid peroxides able to be prepared by the process of the invention are:

t-butyl peroxyacetate,
t-butyl peroxyisobutyrate, cumyl peroxyisobutyrate,
t-butyl peroxypivalate, cumyl peroxypivalate,
t-butyl peroxy-2-ethylhexanoate, cumyl peroxy-2-ethylhexanoate,
t-butyl peroxyneodecanoate, cumyl peroxyneodecanoate,
t-butyl peroxybenzoate,
di-t-butyl diperoxyphthalate,
di-t-butyl diperoxymalonate, di-t-butyl diperoxysuccinate,
di-t-butyl diperoxyglutarate, di-t-butyl diperoxyadipate,
di-t-butyl diperoxyazelate, di-t-butyl diperoxysebacate,
di-t-butyl diperoxyfumarate,
2,5-dimethyl-2,5-di(2-ethylhexanoylperoxy)hexane,
2,5-dimethyl-2,5-di(pivaloylperoxy)hexane,
2,5-dimethyl-2,5-di(neodecanoylperoxy)hexane,
2,5-dimethyl-2,5-di(benzoylperoxy)hexane,
2,5-dimethyl-2,5di(2-ethylhexanoylperoxy)hexyne-3,
1,4-di[$\alpha,\alpha$-dimethyl-$\alpha$(-(t-butylperoxycarbonyl)-methyl]-benzene,
t-butyl peroxy-2-methoxybenzoate, t-butyl peroxy-2-methylbenzoate,
t-butyl peroxy-2-chlorobenzoate, t-butyl peroxy-2-chlorobutyrate,
t-butyl peroxy-2-chlorooctanoate, 2,5-dimethyl-2,-5-di(2-chlorobutyrylperoxy) hexyne-3,
diacetyl, dipropionyl, dibutyryl, diisobutyryl, dipentanoyl,
dihexanoyl, acetyl propionyl, acetyl pentanoyl, di-2-methylpentanoyl, acetyl 2-ethylhexanoyl, acetyl isobutyryl, acetyl isovaleroyl, acetyl 3,5,5,-trimethylhexanoyl, acetyl cyclohexanecarbonyl,
pelargonyl, diisononanoyl, decanoyl, acetyl 2-chloropropionyl, acetyl 2-chlorobutyryl, di-2-chlorobutyryl, and 2-chlorobutyryl m-chlorobenzoyl peroxides.

The lower molecular weight diacyl peroxides are more hazardous in the pure state and are preferably prepared in diluted form using a safety solvent. When each of the moieties R and $R_1$ are greater than 6 carbons, the safety characteristics improve and the solvent may be omitted. Mixtures or mixed diacyl peroxides (prepared in a batch process from a peroxyacid and an acid chloride) can also be processed as long as they are liquid and stable at the processing temperatures. Hence, a diacyl peroxide, normally solid at ambient or room temperature, may be dried if it is a liquid and stable (i.e., does not materially decompose or lose active oxygen content) at an elevated temperature below its decomposition temperature.

The crude product obtained in the batch process prior to the drying step contains a variety of impurities such as acid chlorides, alkyl hydroperoxides, di-t-Butyl peroxide, t-Butyl alcohol, moisture, etc. generated from the side reactions in the reaction step, left behind residually due to incomplete conversions of the raw materials or introduced as impurities along with the raw materials. One or a combination of the following solutions—a buffered sulfite solution (that is, a solution of acetic acid, sodium acetate and sodium sulfite), sodium hydroxide, potassium hydroxide, sodium bicarbonate solutions, or the like, (may be used for the washings) to reduce some of the impurities in the crude product.

The wash steps are followed by physical separation of the emulsified aqueous and organic phases. The crude product after these steps still contains most of the impurities in fair concentrations. Conventional methods, which use chemical drying agents, are effective only in reducing the moisture levels in the product. The other organic impurities remain in the product and, as explained infra, affect product performance adversely in its end applications in the polymer industry. The present process utilizes the relative volatility between the impurities and the parent compound to preferably extract the undesired components of the crude yielding a product of much better quality and activity thus alleviating many of the problems encountered in its use in the polymer industry. The liquid organic peroxides are purified using a convective distillation column—either packed column or with trays—using cooled air having a dew point $\leq -40°$ C. Effects of Impurities, in Peresters, on Radical Polymerizations (1) t BuOOH or Cumene hydroperoxide Can act as a chain transfer agent, since the hydroperoxide hydrogen is readily abstractable. The effect of such chain transfer will be a reduction in molecular weight, and the formation of polymers with peroxidic end groups.

The hydroperoxide is also a problem in recycle type continuous polymerizations such as high pressure ethylene polymerization. Due to its very high thermal stability it may not be decomposed during passage through the reactor, and hence may pass through into the recycle line possibly causing polymerization in this line or the main tank.

Hydroperoxides decompose in the presence of acids or metal salts much more rapidly than do peresters, thus a hydroperoxide may cause problems in a premixed polymerizable formulation by causing it to polymerize during storage if any such acids or metal salts are present as impurities.

(2) di-t (di-t-butyl peroxide)

High temperature peroxide which can cause polymerization in recycle streams as noted in (1)

Di-t is also a good crosslinking agent and when present as impurity could cause undesirable crosslinking during a polymerization.

May also survive, undecomposed during the polymerization process, to cause degradation problems during later high temp service of the product.

(3) $H_2O$

May cause corrosion in reactors, bubbles or poor surfaces in cell cast polymer sheets, and extrusions.

(4) low molecular weight hydrolyzable organic chlorides

May form HCl by hydrolysis, causing corrosion problems.

(5) T-butanol

Mild chain transfer agent, but no serious problems.

(6) Cumene

Inhibitor or retarder-may slow down a polymerization process or prevent polymerization altogether until the cumene has been removed by reaction with free radicals. Hence, cumene works directly against the peroxide.

(6) Volatiles

May cause bubbles or cracks in polymer castings such as cell cast PMMA sheets, and blisters on extrusions from polymers containing such volatiles.

The liquid peroxide products show increased batch yields containing less water (i.e., about 50%) than that found in the conventional prior art batch method. In general, using the present invention the alcohol impurity content has been decreased by up to 75%, the di-t-butyl peroxide impurity content has been decreased by at least 30%, and the product quality has substantially improved.

Environmentally, the air drying column eliminates the solid waste ($MgSO_4$-liquid product) disposal problem since a high percentage of the liquid peroxide is lost when dried with $MgSO_4$ (i.e., 0.5 lb. to 1 lb. product/1 lb. MgSOhd 4). The evolution of $H_2S$ pollutant caused by action of anaerobic bacteria in the presence of $MgSO_4$ is also eliminated.

Figure 2:
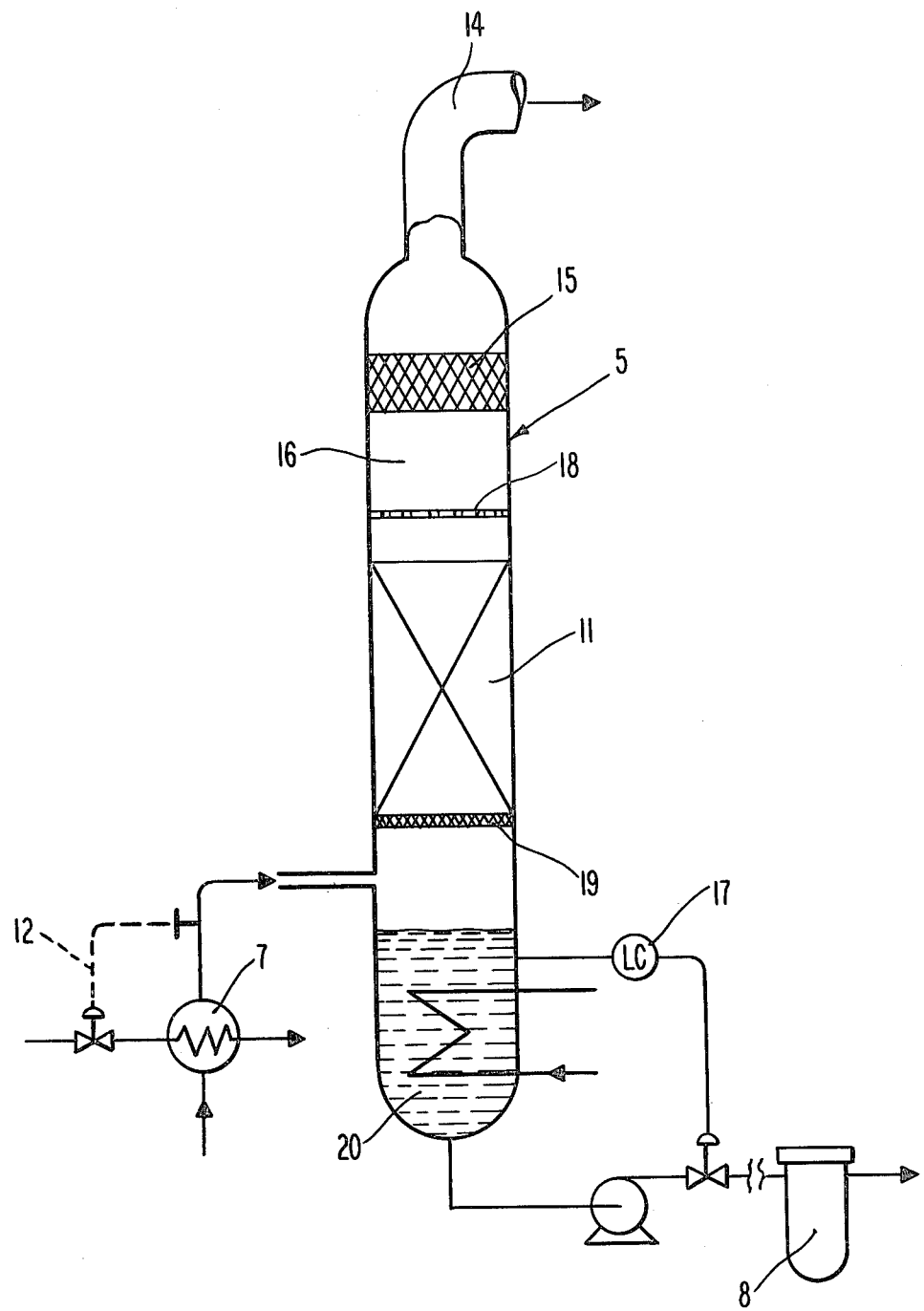

The invention will be better understood by reference to the drawings. FIGS. 1 and 2 are schematic views of one form of apparatus suitable for practicing this invention.

The batch reactants of FIG. 1 are added to reactor 1 where the complete reaction conversion of the acid chloride takes place with the temperature of the reaction mixture being maintained within $\pm 1°$ C. of that desired ($-10°$ C. to $+50°$ C.) and the pH maintained in a range of 10 to 12. The reactor 1 is provided with an efficient agitating means such as stirrer 9 to ensure thorough mixing of the reactants and cooling means 10 to remove the heat of reaction.

The batch product mass is then sent to a washing system that includes one or more washing tanks such as 2 and 3 where the impurities are separated in an aqueous layer and the liquid product in the organic layer. The wet organic product is then sent to a holding tank 4.

From the holding tank 4 the wet product is sprayed into the top of distillation column 5 having packing in section 11. Dry air is cooled to the appropriate temperature in heat exchanger 7 having a temperature regulator 12 for controlling the temperature of the dry air or inert gas; the dry air is then sent via 13 to column 5 below the packing section 11. The dry, cooled air (or inert gas) is passed upwardly in counterflow to the downwardly flowing wet product. The water is removed from the product convectively and is admitted to the atmosphere via 14 if it meets the Government legal pollution standards. The column may have a demister section 15 and a disengaging space 16 in the upper section to provide for greater separation of the organic product from the water so that little, if any, of the product is lost in the atmosphere. The bottom of the column 5 has a sump section 20 where the product is maintained at a desired level by liquid level control 17 to ensure the desired seal and pressure in the vessel. The dry product is then removed to storage tank 6 where it remains until used. An optional filter 8 is connected to tank 6 for further refinement of the liquid peroxide when necessary.

FIG. 2 shows a more detailed purification (or distillation) column for practicing the invention. The crude product obtained after the separation in the final wash step in the process is introduced into the column 5 at the top of the packing. It is advisable to use a liquid distributor plate 18 at the top of the packed bed 11 to ensure efficient operation of the column. Any of the wide variety of packings available commercially, such as, pall rings, berl saddles, etc., could be used to increase the interfacial area between the liquid and gas for efficient mass transfer. Optionally, other types of columns such as bubble cap trays, sieve trays could also be considered for such applications. Packed columns, however, offer greater flexibility with respect to flow rates of liquid and gas. The packing is held in the column on a packing support plate 19 with provisions to ensure efficient distribution of air or inert gas introduced at the bottom of the column. Depending on the types of impurities to be removed, the column can be operated at or below atmospheric pressure. Dry air or inert gas is cooled to the appropriate temperature in heat exchanger 7 having a temperature regulator 12 for controlling the temperature of the dry air, or inert gas the dry air or inert gas is introduced into the column 5 below the packing section 11. The dry, cooled air (or inert gas) is passed upwardly in counterflow to the downwardly flowing crude product. The impurities in the crude product are removed convectively and pass through the column exhaust 14 to the atmosphere.

Optionally, the column exhaust stream 14 could be passed through a scrubber which employs a high boiling organic solvent in countercurrent flow to extract the organic vapors from the gas stream or the column exhaust stream 14 could be passed through a burner to destroy the organic vapors by combustion. These would serve to further minimize the air pollution problems. The column may have a demister section 15 and a disengaging space 16 in the upper section of the column above the distributor plate to prevent physical entrainment of the organic product in the column exhaust stream thereby essentially eliminating product losses to the atmosphere. The bottom of the column has a sump section 20 where the product is maintained at a desired level by liquid level control 17 to ensure the desired seal and pressure in the vessel. The purified product is then removed to a storage tank where it remains until used. Optionally, a product filter 8 is placed in the line for removal of fine, suspended solids thereby providing for further refinement of the liquid peroxide. The flow rates of the crude product and the air depend on the nature of the product being purified. In general, in packed beds, better efficiencies of operation are obtained when good liquid distribution is maintained and the bed is operated in excess of 1 gpm/ft.$^2$ liquid rate. The emission of the liquid peroxide in the column exhaust stream is a function of the liquid/air flow ratio (L/V). At the low L/V ratios (i.e. L/V <0.5 w/w) the product losses are much higher than for high L/V ratios. Hence, this ratio should be high, i.e., greater than 0.5 and preferably about 1 to 2 depending upon the liquid peroxide being recovered.

The diameter of the packed column depends upon the characteristics of the crude product (density, viscosity, etc.) and the flow rate desired for the rectification operation. The height of the packed bed depends upon the number of stages required to reduce the impurities in the product to acceptable levels. For a packed bed employed in distillation operation, the H.E.T.P. (Height Equivalent of A Theoretical Plate) depends upon the type and size of packing material. In the present application the H.E.T.P. was 1.5 ft. The packing size used is critical to ensure proper liquid-gas interfacial contact and depends upon the diameter of the column. In general, for efficient column operation, the ratio of the column diameter to packing size should be in the range 8 to 24.

There are many advantages of the instant invention over the prior art:

1. Extremely low moisture levels (<500 ppm) can be attained by this method.
2. This method is very effective in removing the impurities in crude product thereby generating a product of greater purity, greater activity in polymerization applications.
3. In this method, the moisture present in the product is removed by physical means i.e. mass transfer from liquid to vapor phase (as opposed to the exothermic chemical reaction in the prior art method). The evaporation of moisture serves to cool the product as it flows downwardly in the column thereby greatly enhancing the safety of operation.
4. The productivity ofk the plant is significantly improved as this step does not act as a bottleneck in the process.
5. There is significant improvement in the yields/batch of product as the losses of product by adsorption on the filter cake are eliminated.
6. The problem of disposal of the filter cake is eliminated thereby greatly alleviating the problem of environmental pollution.

The following examples merely illustrate the invention and are not meant to limit the practice of this invention thereto.

The products set forth in the Examples of TABLE A were prepared by the following general batch procedure. The reactants constituting a batch were reacted in reactor 1 in a temperature range of −10° C. to +50° C. and a pH greater than 10. The reactor was vigorously agitated to ensure intimate mixing for a complete reaction. The reaction product was washed in tanks 2 and 3 and some of the wet products were dried conventionally using MgSO$_4$ filter cakes and others were dried in the convective distillation column 5 as previously described.

TABLE A

| Ex. | Product | MgSO$_4$ Filtered Output (Part) | Column Dried Output (Parts) | % increase |
|---|---|---|---|---|
| 1. | t-Butyl Perbenzoate | 1.00 | 1.20 | 20% |
| 2. | t-Butyl Peroctoate | 1.00 | 1.11 | 11% |
| 3. | t-Butyl Peroxyneodecanoate (75% in odorless mineral spirits) | 1.00 | 1.25 | 25% |
| 4. | t-Butyl Peroxypivalate (75% in odorless mineral spirits) | 1.00 | 1.11 | 11% |

Note that the figures in TABLE A are an average of about 100 runs of the particular batch process. The average column dried output is compared to the MgSO$_4$ filtered output which is 1.00 part or 100%. In every instance, the column drying showed an at least 11% increase in output over the prior art MgSO$_4$ filtered output. This is a significant increase, especially in commercial operations.

TABLE B

COMPARISON OF PRODUCT QUALITY
MgSO₄ DRIED VS COLUMN DRIED

| Ex. | Product | MgSO₄ Dried | | | | | Column Dried | | | |
|---|---|---|---|---|---|---|---|---|---|---|
| | | Assay | tBHP | Cl⁻ | di-t | tBA | Assay | tBHP | Cl⁻ | di-t | tBA |
| 1 | t-Butyl Perbenzoate | 8.7 | 0.15 | 0.003 | 0.15 | 0.21 | 99.6 | <0.005 | 0.001 | <0.05 | 0.1 |
| 2 | t-Butyl Peroctoate | 97.7 | >0.05 | 0.006 | 0.12 | 0.75 | 99.0 | <0.05 | 0.002 | <0.05 | 0.4 |
| 3 | t-Butyl Peroxyneodecanoate (75% in odorless mineral spirits) | 75 | <0.05 | 0.08 | 0.2 | 0.35 | 75 | <0.05 | 0.02 | <0.05 | 0.1 |
| 4 | t-Butyl Peroxypivalate (75% in odorless mineral spirits) | 75 | 0.10 | 0.02 | <0.05 | 0.1 | 75 | <0.05 | 0.006 | <0.05 | <0.05 |

TABLE C

COMPARISON OF INITIATOR EFFICIENCY AT DIFFERENT IMPURITY LEVELS

Experimental Work was carried out to test the efficiency of α-Cumyl peroxypivalate with different impurity levels in Vinyl Chloride suspension polymerization reactions. The polymerizations were carried out in a pH 10 suspension at 55° C. with Io (initiator concentration) 0.15 phm (pure basis). The time to obtain a pressure drop (~70% conversion), Tp, was used as the criterion for measuring polymerization efficiency. The details are shown below:

| Sample | Impurity level (% cumene) | Tp, mins. | Improvement in Efficiency |
|---|---|---|---|
| α-Cumyl peroxypivalate (Sample I) | 1.7 | 250 | — |
| α-Cumyl peroxy-Pivalate (Sample II) | 0.52 | 170 | 32% |

α-Cumyl peresters can be purified using such a system when it is operated under sub atmospheric conditions to generate a product of improved activity in Vinyl Chloride polymerization reactions as indicated in the Examples in Table C.

TABLE D

| | Di(3,5,5-trimethylhexaneyl)peroxide Column Purification | | | | |
|---|---|---|---|---|---|
| Run # | Air Flow rate scfm | Liquid Flow rate gm/min. | % Assay | % Cl⁻ | % H₂O |
| A CRUDE (BEFORE COLUMN) | — | — | 75.8 | 0.35 | 0.50 |
| B PURIFIED (AFTER COLUMN) | 1.55 | 7.3 | 78.0 | 0.22 | <0.1 |

Table D shows the purification of a diacyl peroxide by the column stripping process of this invention.

What is claimed:

1. In a batch process for the manufacture of a peroxy compound having the formula $(R)_y$

wherein:
(a) x, y and n are 1 or 2;
(b) when x is 2, y is 1 and n is 2;
(c) when y is 2, x is 1 and n is 2;
(d) when x, y and n are 1, R is selected from the group consisting of a primary, secondary, or tertiary alkyl of 1 to 17 carbons, aryl of 6 to 14 carbons, and cycloalkyl of 3 to 12 carbons, said alkyl and cycloalkyl groups may be substituted by halogen, alkoxy or aryl, said aryl group may be substituted by halogen, alkoxy or alkyl; and
R' is selected from the group consisting of tertiary alkyl of 4 to 12 carbons, tertiary aralkyl of 9 to 18 carbons, tertiary cycloalkyl of 6 to 12 carbons &

wherein R₁ is independently selected from the definition of R except for tert.-alkyl;
(e) when x is 2, R is a diradical selected from the group consisting of alkylene of 1 to 16 carbons, arylene of 6 to 14 carbons, cycloalkylene of 3 to 12 carbons, and aralkylene of 7 to 18 carbons; and R' is the same as (d) except for

and
(f) when y is 2, R' is a di-tertiary diradical selected from alkylene of 6 to 16 carbons, aralkylene of 12 to 18 carbons, cycloalkylene of 7 to 12 carbons and alkynylene of 6 to 16 carbons and R is the same as (d); which comprises:
(1) Charging a batch reactor with

and R¹ (OOH)ₙ in molar equivalent proportions selected from the group consisting of:
(i) 0.9 to 1.1 molar equivalents of

and 0.4 to 0.6 molar equivalent of H₂O₂ or 0.9 to 1.1 molar equivalent of R¹OOH or (ii) 0.9 to 1.1 molar equivalent of

and 0.4 to 0.6 molar equivalent of $R^1(OOH)_2$, and (iii) 0.9 to 1.1 molar equivalent of

and 1.8 to 2.2 molar equivalent of $R^1OOH$ and an amount of an aqueous alkali metal hydroxide to maintain a pH greater than 10 and reacting this batch while stirring at a temperature range of about $-10°$ C. to $+50°$ C. for a sufficient time to complete the reaction; and (2) washing the reaction batch with an aqueous solution to remove impurities from the liquid organic product and adjust the pH to neutral; the improvement which comprises (3) purifying the liquid organic product in a countercurrent packed distillation column wherein the crude product is dispersed at the top of the column over the column packing and the purified product is removed from the bottom of the column, the crude product is countercurrently contacted with air or an inert gas admitted to the bottom of the column above a product sump in the bottom of the column wherein the product is maintained at a desired level to prevent exhaust of air at the bottom the overhead gas stream is released to the atmosphere, the ratio of the downwardly flowing crude product to the upwardly flowing air or inert gas depends on the nature of the product being purified.

2. The batch process of claim 1 wherein the liquid peroxide is selected from the group consisting of t-Butyl perbenzoate, t-Butyl peroctoate, t-butyl peroxyneodecanoate, t-butyl peroxypivalate, cumyl peroxyneodecanoate and cumyl peroxypivalate.

3. The batch process of claim 1 wherein the purified product from step (3) is passed further through a polishing filter to remove the residual suspended solids left behind by the evaporation of moisture in the purification process.

* * * * *